US006363277B1

(12) United States Patent
Dooley et al.

(10) Patent No.: US 6,363,277 B1
(45) Date of Patent: Mar. 26, 2002

(54) CARDIAC RHYTHM MANAGEMENT SYSTEM WITH DIFFERENTIAL SENSING CHANNEL

(75) Inventors: Michael W. Dooley, St. Paul; Ronald Balczewski, Roseville; William J. Linder, Golden Valley, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/378,403

(22) Filed: Aug. 20, 1999

(51) Int. Cl.[7] ................................................ A61N 1/36
(52) U.S. Cl. .................................................... 607/9
(58) Field of Search ...................... 607/5–33; 600/509, 600/510

(56) References Cited

U.S. PATENT DOCUMENTS

| 4,023,046 A | 5/1977 | Renirie ........................ 307/360 |
| 4,043,347 A | 8/1977 | Renirie ..................... 128/419 PG |
| 4,649,931 A | 3/1987 | Beck ............................. 128/708 |
| 5,318,597 A | 6/1994 | Hauck et al. .................. 607/20 |
| 5,606,320 A | 2/1997 | Kleks ........................... 341/161 |
| 5,729,230 A | 3/1998 | Jensen et al. ................ 341/143 |
| 5,902,249 A | * 5/1999 | Lyster |

* cited by examiner

Primary Examiner—Scott M. Getzow
(74) Attorney, Agent, or Firm—Schwegman, Lundberg, Woessner & Kluth, P.A.

(57) ABSTRACT

A differential discrete-time signal processing channel differentially processes cardiac signals in an implantable cardiac rhythm management device. Such signal processing effectively uses downsampling to uses lower bias currents, thereby saving power and prolonging the life of the implanted device, and also reduces clock feedthrough, provides a wider dynamic range and better rejection of power supply noise. The device includes a continuous-time buffer, a decimator/averager and/or other filter and/or amplifier circuits, and an analog-to-digital converter, each configured for processing differential signals. The device also includes an operational transconductance amplifier (OTA), for the discrete-time differential signal processing. The OTA provides, among other things, an output common mode adjustment circuit and an offset compensation circuit.

29 Claims, 10 Drawing Sheets

CARDIAC RHYTHM MANAGEMENT SYSTEM WITH DIFFERENTIAL SENSING CHANNEL

TECHNICAL FIELD

The present system relates generally to cardiac rhythm management systems and particularly, but not by way of limitation, to a cardiac rhythm management system providing, among other things, a differential sensing channel.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is in acquiring the intrinsic electrical signals produced by the heart, which are referred to as "cardiac signals" or "heart signals." Such cardiac signals include, among other things, electrical depolarizations associated with heart chamber contractions and electrical repolarizations associated with heart chamber expansions. Decisions regarding the delivery and/or withholding of cardiac rhythm management therapy are often based at least in part on information included within such cardiac signals. Moreover, cardiac signals may include information indicating the efficacy of therapy that has already been delivered. Therefore, acquisition of cardiac signals is one important task of implantable or external cardiac rhythm management systems.

One type of circuit used in acquiring cardiac signals includes a linear preamplifier, receiving signals from first and second cardiac electrodes and providing a single-ended output signal based thereon. The linear preamplifier is followed by a switched-capacitor signal processing channel that performs single-ended discrete time signal processing including analog-to-digital conversion. Switched-capacitor signal processing circuits perform signal processing using charges that are sampled onto capacitors during a "clock period." Such a signal processing circuit, however, presents several drawbacks that limit its usefulness in an implantable cardiac rhythm management device, as discussed below.

For example, a switched-capacitor filter circuit utilizes an operational transconductance amplifier (OTA) that typically has an intrinsic offset voltage. The offset voltage may introduce errors into cardiac signals being processed. In order to accommodate such offset voltages and to decrease the effect of offset errors, autozeroing circuits are typically used in the single-ended signal processing channel. An autozeroing circuit works by periodically prestoring a charge associated with the offset voltage on a signal processing capacitor (i.e., "autozeroing"). Then, subsequent single-ended signal processing is performed using differences between the prestored charge and the charge associated with the cardiac signal or other desired signal of interest.

Autozeroing is typically performed during the same length of time that is allocated for the clock period during which the cardiac signal is sampled. Moreover, during autozeroing the gain and feedback configuration of the operational amplifier and the load capacitance being driven typically impose more strenuous demands on the amplifier than does normal sampling of the cardiac or other signal being processed. As a result, proper autozeroing operation of the operational amplifier typically dictates the magnitude of the bias current used in the operational amplifier. However, in power-sensitive applications, such as battery-powered implanted medical devices, larger currents cause the battery to drain faster. This reduces the useful life of the implanted device. A shorter device life results in more frequent replacement of the implanted medical device, with all its attendant costs and risk of complications. Thus, there is a need for improved autozeroing and/or other cardiac signal processing techniques that consumes less power, in order to provide more economical medical treatment, and to reduce the risks associated with replacement of an implanted cardiac rhythm management or other implanted medical device.

SUMMARY OF THE INVENTION

This document describes, among other things, portions of a differential signal processing channel for differentially processing signals, such as cardiac signals in an implantable cardiac rhythm management device. The differential signal processing channel offers many advantages over single-ended discrete-time processing of cardiac signals using conventional autozeroing techniques. For example, the above-described differential signal processing techniques allow the use of lower bias currents in the active circuits used in discrete time signal processing. This saves power, thereby extending the useful life of the implanted device before explantation and replacement becomes necessary.

The differential signal processing techniques also reduce the effects of clock feedthrough of the switches used in the switched-capacitor circuits, provide a wider dynamic range for the cardiac signals being acquired, and provide better rejection of power supply noise. This document also describes an operational transconductance amplifier (OTA), capable of use in the discrete-time differential signal processing channel. The OTA provides, among other things, an output common mode adjustment circuit and an offset compensation circuit.

In one embodiment, a cardiac rhythm management system includes an implantable cardiac rhythm management (CRM) device. The CRM device includes an interface circuit, including first and second inputs and including first and second outputs providing an analog differential output signal based on the signals at the first and second inputs. The CRM device also includes a discrete-time differential signal processing channel providing a digitized output signal based at least in part on an analog differential output signal received from the first and second outputs of the interface circuit.

This document also discloses an operational transconductance amplifier (OTA) circuit capable of use in the discrete-time differential signal processing channel. The OTA circuit includes a differential-voltage-to-differential-current converter circuit, a common mode adjustment circuit, and an offset correction circuit.

This document further discloses a method of acquiring cardiac signals. Cardiac signals are received at first and second cardiac electrodes. The cardiac signals are communicated to an implantable cardiac rhythm management device. The cardiac signals received from the first and second cardiac electrodes are buffered to provide a differential buffered signal. The differential buffered signal is processed differentially and in discrete-time. A digitized output signal is provided based on the processed differential signal.

In one embodiment, the disclosed signal processing methods include receiving a differential input voltage between first and second inputs and providing a differential output current, based on the differential input voltage, at first and second outputs. A common mode voltage at the first and second outputs is adjusted. An offset in the differential output current at the first and second outputs is compensated. These and other aspects of the present system and methods will become apparent upon reading the following detailed description and viewing the accompanying drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components. In this document, "and/or" refers to non-exclusive "or" (e.g., "A and/or B" includes each of "A but not B," "B but not A," and "A and B").

The present methods and apparatus will be described in applications involving implantable medical devices including, but not limited to, implantable cardiac rhythm management systems such as pacemakers, cardioverter/defibrillators, pacer/defibrillators, and biventricular or other multi-site coordination devices. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders.

General System Overview and Examples

Figure 1:
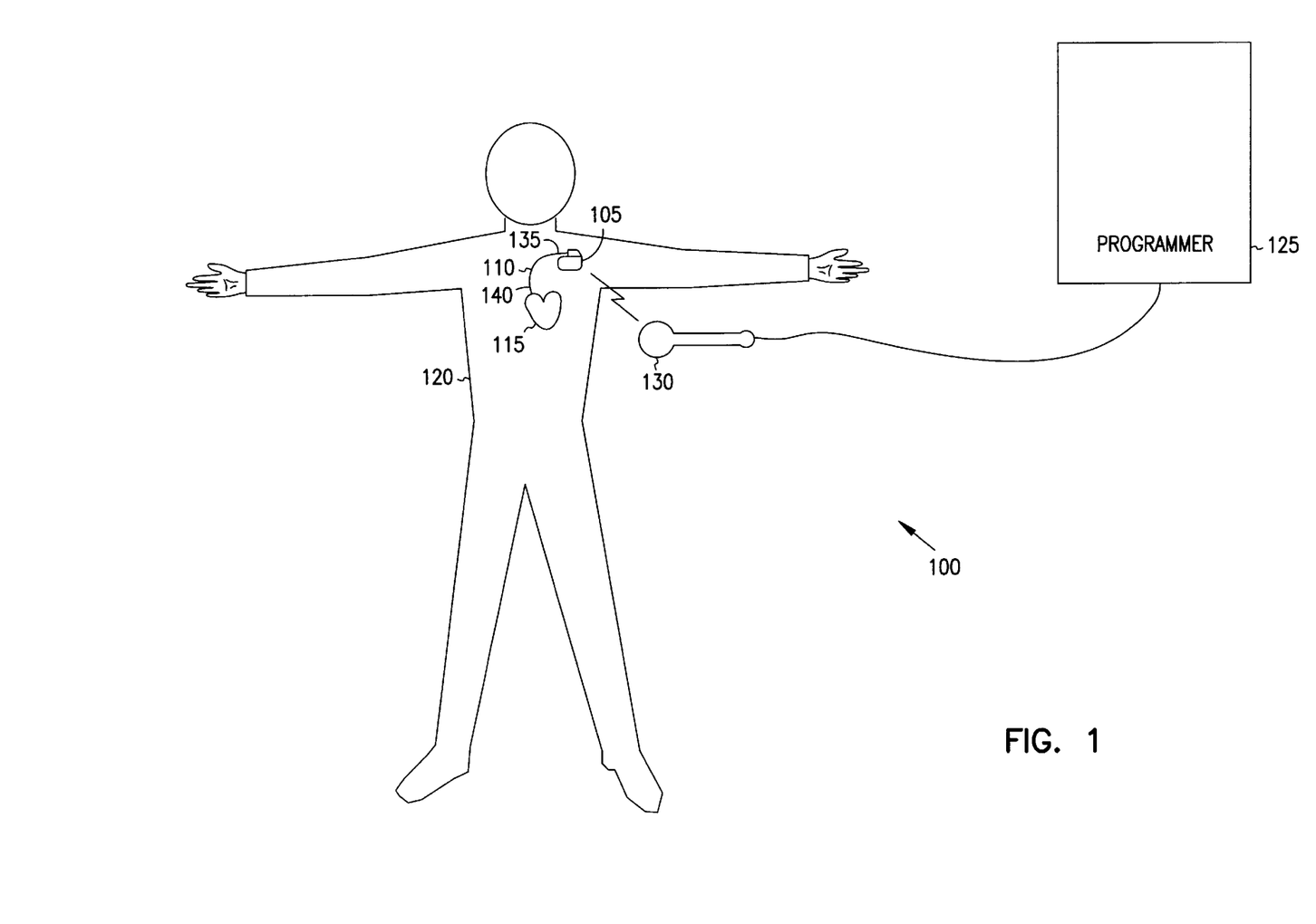
FIG. 1 is a schematic drawing illustrating generally one embodiment of portions of a cardiac rhythm management system and an environment in which it is used.

This document describes, among other things, a cardiac rhythm management system with at least one differential sensing channel. FIG. 1 is a schematic drawing illustrating generally, by way of example, but not by way of limitation, one embodiment of portions of a cardiac rhythm management system 100 and an environment in which it is used. In FIG. 1, system 100 includes an implantable cardiac rhythm management device 105, also referred to as an electronics unit, which is coupled by an intravascular endocardial lead 110, or other lead, to a heart 115 of patient 120. System 100 also includes an external programmer 125 providing wireless communication with device 105 using a telemetry device 130. Catheter lead 110 includes a proximal end 135, which is coupled to device 105, and a distal end 140, which is coupled to one or more portions of heart 115.

Figure 2:
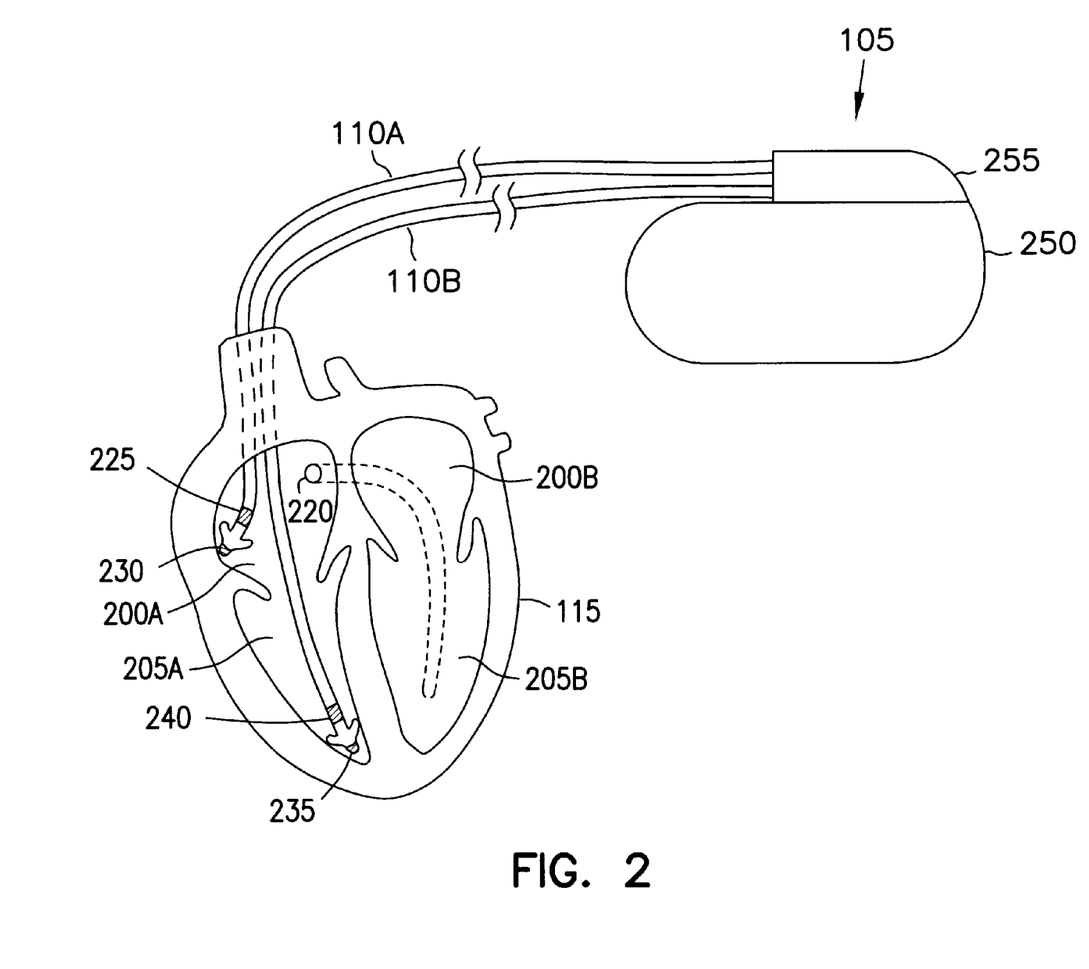
FIG. 2 is a schematic drawing illustrating generally one embodiment of a cardiac rhythm management device coupled by leads to a heart.

FIG. 2 is a schematic drawing illustrating generally, by way of example, but not by way of limitation, one embodiment of device 105 coupled by leads 110A–B to heart 115, which includes a right atrium 200A, a left atrium 200B, a right ventricle 205A, a left ventricle 205B, and a coronary sinus 220 extending from right atrium 200A. In this embodiment, atrial lead 110A includes electrodes (electrical contacts) disposed in, around, or near an atrium 200 of heart 115, such as ring electrode 225 and tip electrode 230, for sensing signals and/or delivering pacing therapy to the atrium 200. Lead 110A optionally also includes additional electrodes, such as for delivering atrial and/or ventricular cardioversion/defibrillation and/or pacing therapy to heart 115.

In FIG. 2, a ventricular lead 110B includes one or more electrodes, such as tip electrode 235 and ring electrode 240, for delivering sensing signals and/or delivering pacing therapy. Lead 110B optionally also includes additional electrodes, such as for delivering atrial and/or ventricular cardioversion/defibrillation and/or pacing therapy to heart 115. Device 105 includes components that are enclosed in a hermetically-sealed can 250. Additional electrodes may be located on the can 250, or on an insulating header 255, or on other portions of device 105, for providing unipolar pacing and/or defibrillation energy in conjunction with the electrodes disposed on or around heart 115. Other forms of electrodes include meshes and patches which may be applied to portions of heart 115 or which may be implanted in other areas of the body to help "steer" electrical currents produced by device 105. In one embodiment, one of atrial lead 110A or ventricular lead 110B is omitted, i.e., a "single chamber" device is provided, rather than the dual chamber device illustrated in FIG. 2. In another embodiment, additional leads are provided for coupling device 105 to other heart chambers and/or other locations in the same heart chamber as one or more of leads 110A–B. The present method and apparatus will work in a variety of configurations and with a variety of electrical contacts or "electrodes."

Example Cardiac Rhythm Management Device

Figure 3:
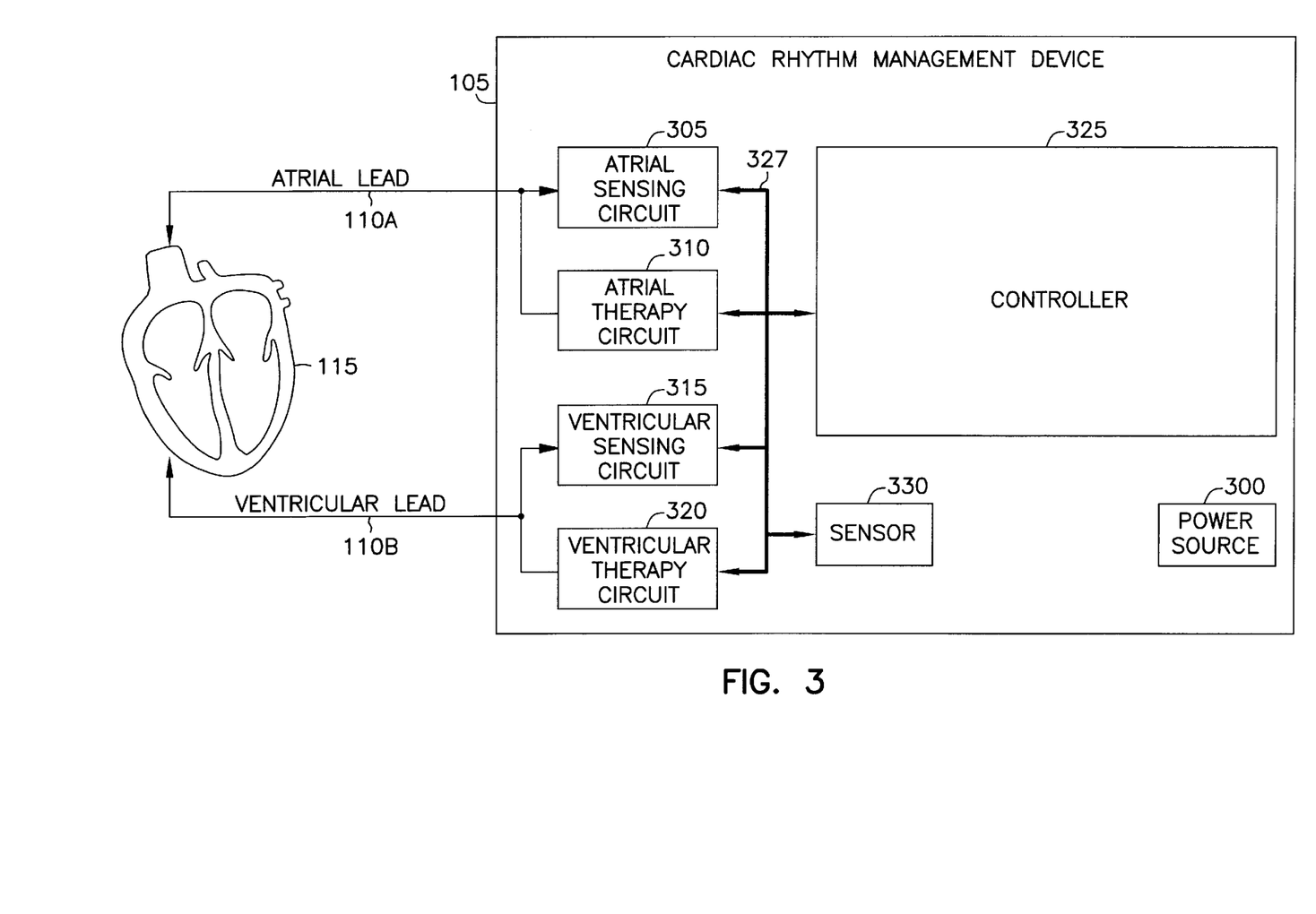
FIG. 3 is a schematic diagram illustrating one embodiment of portions of a cardiac rhythm management device, which is coupled to a heart, and certain aspects of the device.

FIG. 3 is a schematic diagram illustrating generally, by way of example, but not by way of limitation, one embodiment of portions of device 105, which is coupled to heart 115. Device 105 includes a power source 300, an atrial sensing circuit 305, an atrial therapy circuit 310, a ventricular sensing circuit 315, a ventricular therapy circuit 320, and a controller 325. In one embodiment, device 105 also includes a sensor 330 for adjusting the rate at which therapy is delivered.

Atrial sensing circuit 305 is coupled by atrial lead 110A to heart 115 for receiving, sensing, and/or detecting electrical atrial heart signals. Such atrial heart signals include atrial activations (also referred to as atrial depolarizations or P-waves), which correspond to atrial contractions. Such atrial heart signals include normal atrial rhythms, and abnormal atrial rhythms including atrial tachyarrhythmias, such as atrial fibrillation, and other atrial activity. Atrial sensing circuit 305 provides one or more signals to controller 325, via node/bus 327, based on the received atrial heart signals.

In one embodiment, atrial therapy circuit 310 provides atrial pacing therapy, as appropriate, to electrodes located at or near one of the atria 200 of heart 115 for obtaining resulting evoked atrial depolarizations. In a further embodiment, atrial therapy circuit 310 also provides cardioversion/defibrillation therapy, as appropriate, to electrodes located at or near one of the atria 200 of heart 115, for terminating atrial fibrillation and/or other atrial tachyarrhythmias.

Ventricular sensing circuit 315 is coupled by ventricular lead 110B to heart 115 for receiving, sensing, and/or detecting electrical ventricular heart signals, such as ventricular activations (also referred to as ventricular depolarizations or R-waves), which correspond to ventricular contractions. Such ventricular heart signals include normal ventricular rhythms, and abnormal ventricular rhythms, including ventricular tachyarrhythmias, such as ventricular fibrillation, and other ventricular activity. Ventricular sensing circuit 315 provides one or more signals to controller 325, via node/bus 327, based on the received ventricular heart signals.

In one embodiment, ventricular therapy circuit 320 provides ventricular pacing therapy, as appropriate, to electrodes located at or near one of the ventricles 205 of heart 115 for obtaining resulting evoked ventricular depolarizations. In a further embodiment, ventricular therapy circuit 320 also provides cardioversion/defibrillation therapy, as appropriate, to electrodes located at or near one of the ventricles 205 of heart 115, for terminating ventricular fibrillation and/or other ventricular tachyarrhythmias.

Controller 325 controls the delivery of therapy by atrial therapy circuit and/or ventricular therapy circuit 320 and/or other circuits, based on heart activity signals received from atrial sensing circuit 305 and ventricular sensing circuit 315, as discussed below. Controller 325 includes various modules, which are implemented either in hardware or as one or more sequences of steps carried out on a microprocessor or other controller. Such modules are illustrated separately for conceptual clarity; it is understood that the various modules of controller 325 need not be separately embodied, but may be combined and/or otherwise implemented, such as in software/firmware.

In general terms, sensing circuits 305 and 315 sense electrical signals from heart tissue in contact with the catheter leads 110A–B to which these sensing circuits 305 and 315 are coupled. Sensing circuits 305 and 315 and/or controller 325 process these sensed signals. Based on these sensed signals, controller 325 issues control signals to therapy circuits, such as ventricular therapy circuit 320, if necessary, for the delivery of electrical energy (e.g., pacing and/or defibrillation pulses) to the appropriate electrodes of leads 110A–B. Controller 325 may include a microprocessor or other controller for execution of software and/or firmware instructions. The software of controller 325 may be modified (e.g., by remote external programmer 125) to provide different parameters, modes, and/or functions for the implantable device 105 or to adapt or improve performance of device 105.

In one further embodiment, one or more sensors, such as sensor 330, may serve as inputs to controller 325 for adjusting the rate at which pacing or other therapy is delivered to heart 115. One such sensor 330 includes an accelerometer that provides an input to controller 325 indicating increases and decreases in physical activity, for which controller 325 increases and decreases pacing rate, respectively. Another such sensor includes an impedance measurement, obtained from body electrodes, which provides an indication of increases and decreases in the patient's respiration, for example, for which controller 325 increases and decreases pacing rate, respectively. Any other sensor 330 providing an indicated pacing rate can be used.

Example Sensing Circuit

Figure 4:
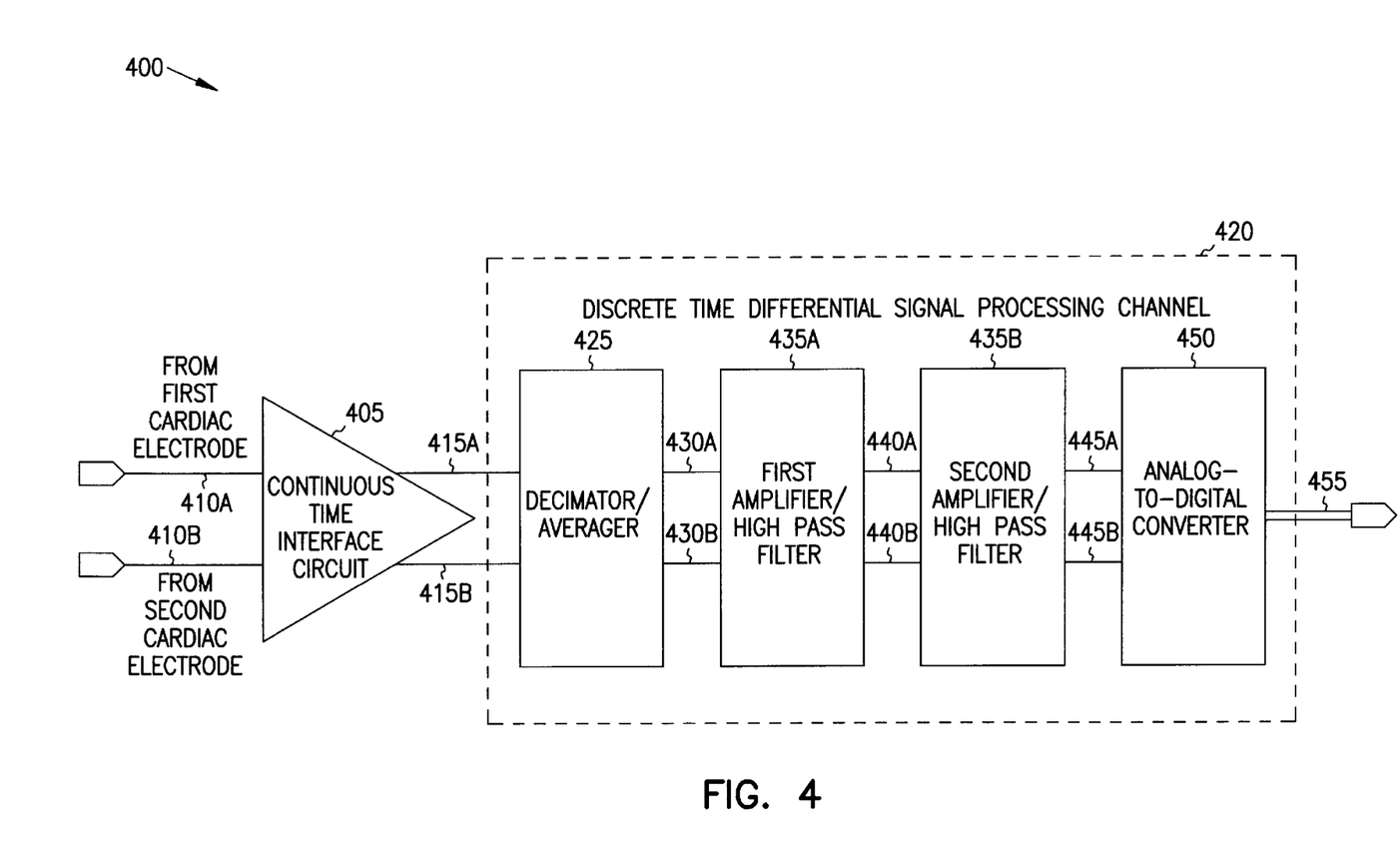
FIG. 4 is a schematic/block diagram illustrating generally one embodiment of portions of a sensing circuit.

FIG. 4 is a schematic/block diagram illustrating generally, by way of example, but not by way of limitation, one embodiment of portions of a sensing circuit 400, such as atrial sensing circuit 305 or ventricular sensing circuit 315. In one embodiment, sensing circuit 400 includes a continuous time buffer/interface circuit 405, such as a linear preamplifier. Interface circuit 405 includes first and second inputs, at respective nodes 410A–B. The first and second inputs of interface circuit 405 receive cardiac signals from first and second cardiac electrodes such as, for example, from tip electrode 235 and ring electrode 240, respectively, which are associated with ventricular lead 11B, or from other electrodes associated with atrial lead 110A or associated with another cardiac lead. Interface circuit 405 also includes first and second outputs, at respective nodes 415A–B, providing a differential output signal based on the differential input signal at input nodes 410A–B. In one embodiment, interface circuit 405 provides a highpass pole at a 3 dB frequency of approximately 10 Hz, a first lowpass pole at a 3 dB frequency of approximately 300 Hz, and a second lowpass pole at a 3 dB frequency of approximately 700 Hz.

This embodiment of sensing circuit 400 also includes a discrete time differential signal processing channel 420, which receives the differential output signal from interface circuit 405 at first and second inputs of a filter, such as decimator/averager 425, at respective nodes 415A–B. The inputs of decimator/averager 425 sample the continuous time cardiac signal from interface circuit 405, and provides a differential output signal at nodes 430A–B. In this embodiment, the sampled-data differential output signal at nodes 430A–B is based a plurality of such input samples at nodes 415A–B. Thus, in this embodiment, the frequency of output samples at nodes 430A–B is lower than the frequency of samples at nodes 415A–B as the result of the downsampling function performed by decimator/averager 425.

In this embodiment, discrete time differential signal processing channel 420 also includes at least one amplifier and/or filter, such as first and second amplifiers/highpass filters 435A–B, which further perform differential discrete time signal processing on the cardiac signals as these signals propagate from nodes 430A–B to 440A–B to 445A–B. After this discrete-time signal processing on the differential signals, analog-to-digital (A/D) converter 450 provides at, node/bus 455, a digital representation of the processed cardiac signal received at inputs 445A–B.

Figure 5:
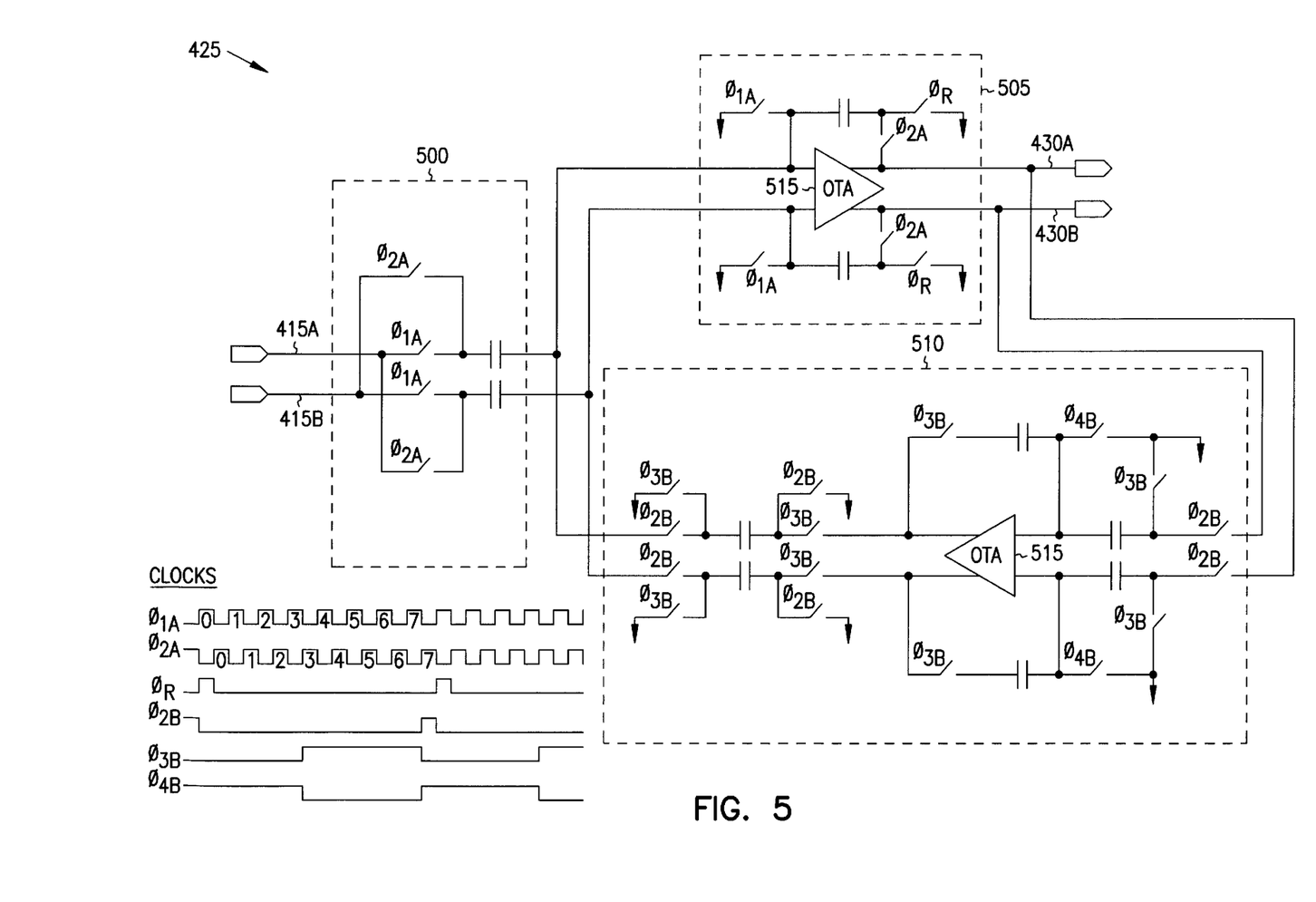
FIG. 5 is a schematic diagram illustrating one embodiment of portions of a differential-signal discrete time decimator/averager.

FIG. 5 is a schematic diagram illustrating generally, by way of example, but not by way of limitation, one embodiment of portions of a differential-signal discrete time decimator/averager 425. In this embodiment, decimator/averager 425 includes an input/sampling stage 500, an integration/averaging stage 505, and an offset-compensation or other highpass feedback integration stage 510. Each of integration/averaging stage 505 and offset-compensation stage 510 include active circuitry such as an operational transconductance amplifier (OTA) 515, one embodiment of which is discussed further below. FIG. 5 also illustrates one embodiment of the relationship between the clock phases $\phi_{1A}$, $\phi_{2A}$, $\phi_R$, $\phi_{2B}$, $\phi_{3B}$, and $\phi_{4B}$ (the corresponding switches are closed when the clock is "high" and open when the clock is "low."). In this embodiment, integration/averaging stage 505 averages eight samples from input/sampling stage 500 before being reset by the switches associated with reset clock $\phi_R$. In one embodiment, integration/averaging stage 505 provides a highpass pole at a 3 dB frequency of approximately 10 Hz, and a lowpass pole at a 3 dB frequency of approximately 100 Hz.

Figure 6A:
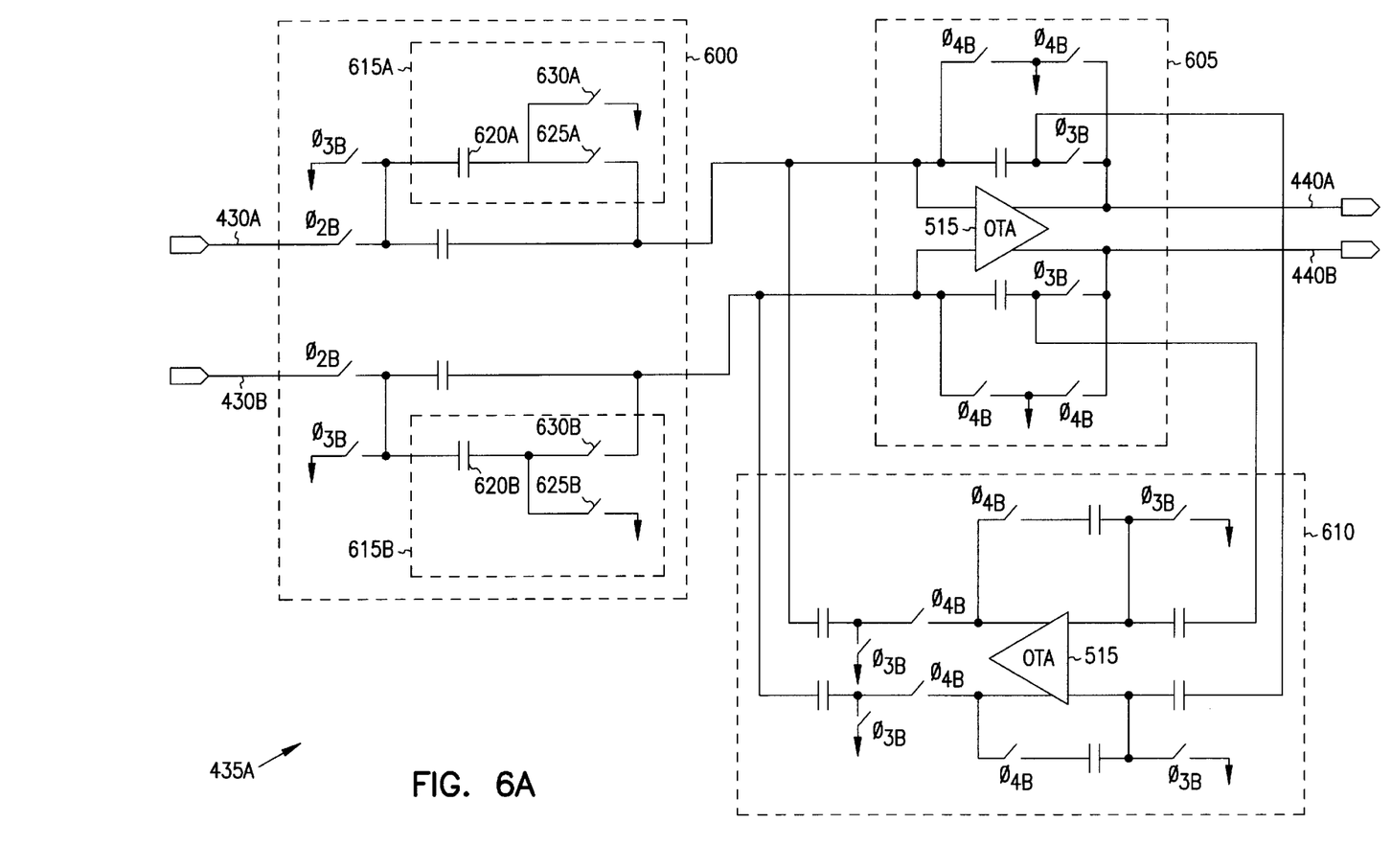
FIG. 6A is a schematic diagram illustrating one embodiment of portions of an amplifier/highpass filter for processing differential signals.

FIG. 6A is a schematic diagram illustrating generally, by way of example, but not by way of limitation, one embodiment of portions of amplifier/highpass filter 435A for processing differential signals. In this embodiment, amplifier/highpass filter 435A includes an input/sampling circuit 600, a feedforward integration circuit 605, and a feedback integration circuit 610, with clock phases as illustrated in FIG. 5. Input/sampling circuit 600 receives the differential signal provided by decimator/averager 425. It includes gain adjustment circuits 615A–B. Each gain adjustment circuit 615A–B includes one or more capacitors 620A–B, one terminal of which is connected either to the feedforward integration circuit 605, through one of switches 625A–B, or to a reference/ground voltage, through the other one of switches 630A–B (e.g., either switch 625A is closed, or else switch 630A is closed, depending on the desired gain). By configuring additional gain adjustment circuits 620 in parallel with those shown, different combinations of gain are obtained by appropriately setting the corresponding switches 625 and 630. In one embodiment, amplifier/highpass filter 435A provides a highpass pole at a 3 dB frequency of approximately 10 Hz.

Figure 6B:
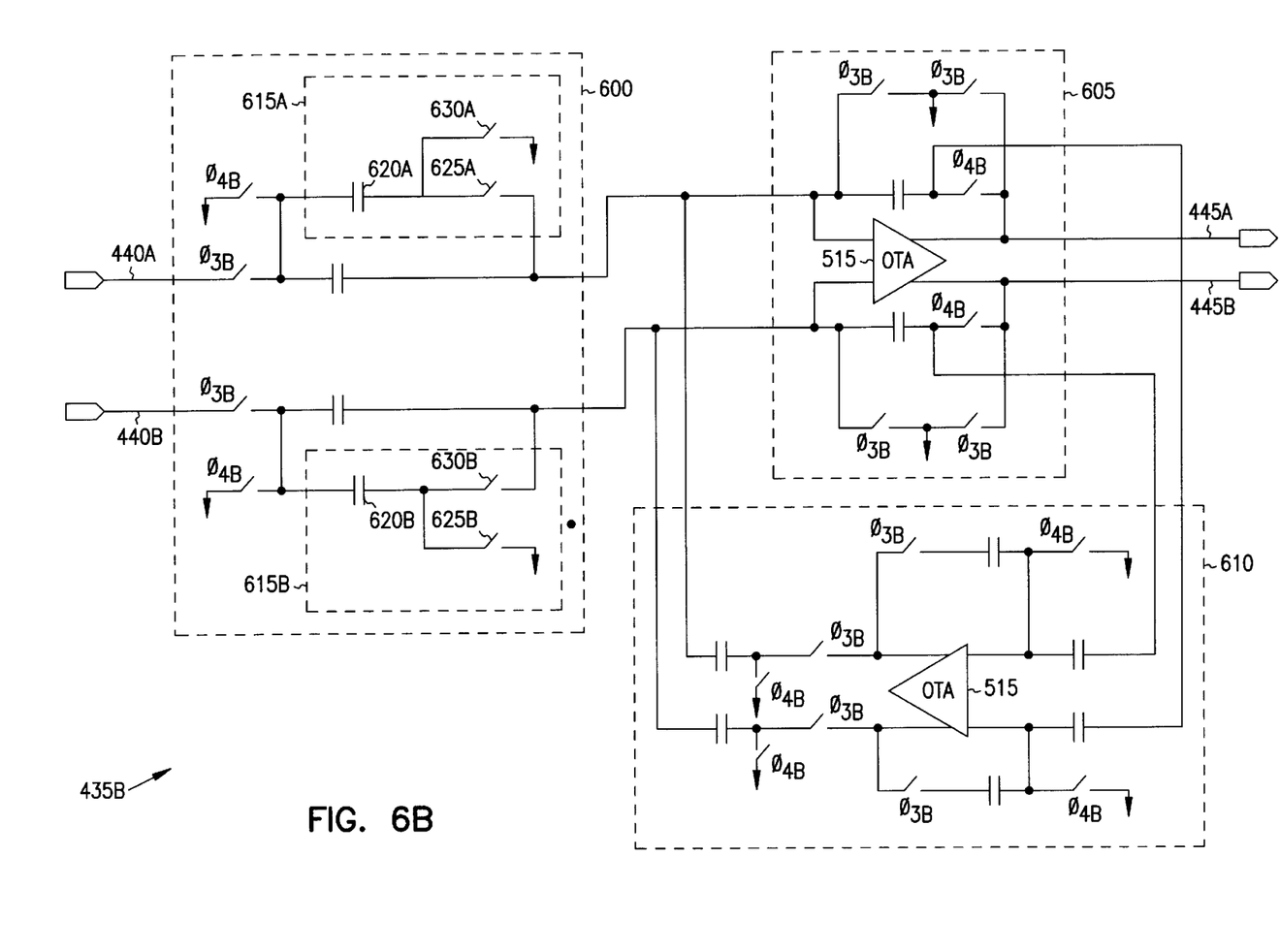
FIG. 6B is a schematic diagram illustrating another embodiment of portions of an amplifier/highpass filter for processing differential signals.

FIG. 6B is a schematic diagram illustrating generally, by way of example, but not by way of limitation, one embodiment of portions of amplifier/highpass filter 435B for processing differential signals. FIG. 6B is similar to FIG. 6A, except for differently phased clocks and that different configurations of gain adjustment circuits can be used. The clocks in FIG. 6B are also illustrated in FIG. 5. In one embodiment, amplifier/highpass filter 435B provides a highpass pole at a 3 dB frequency of approximately 10 Hz.

Figure 7:
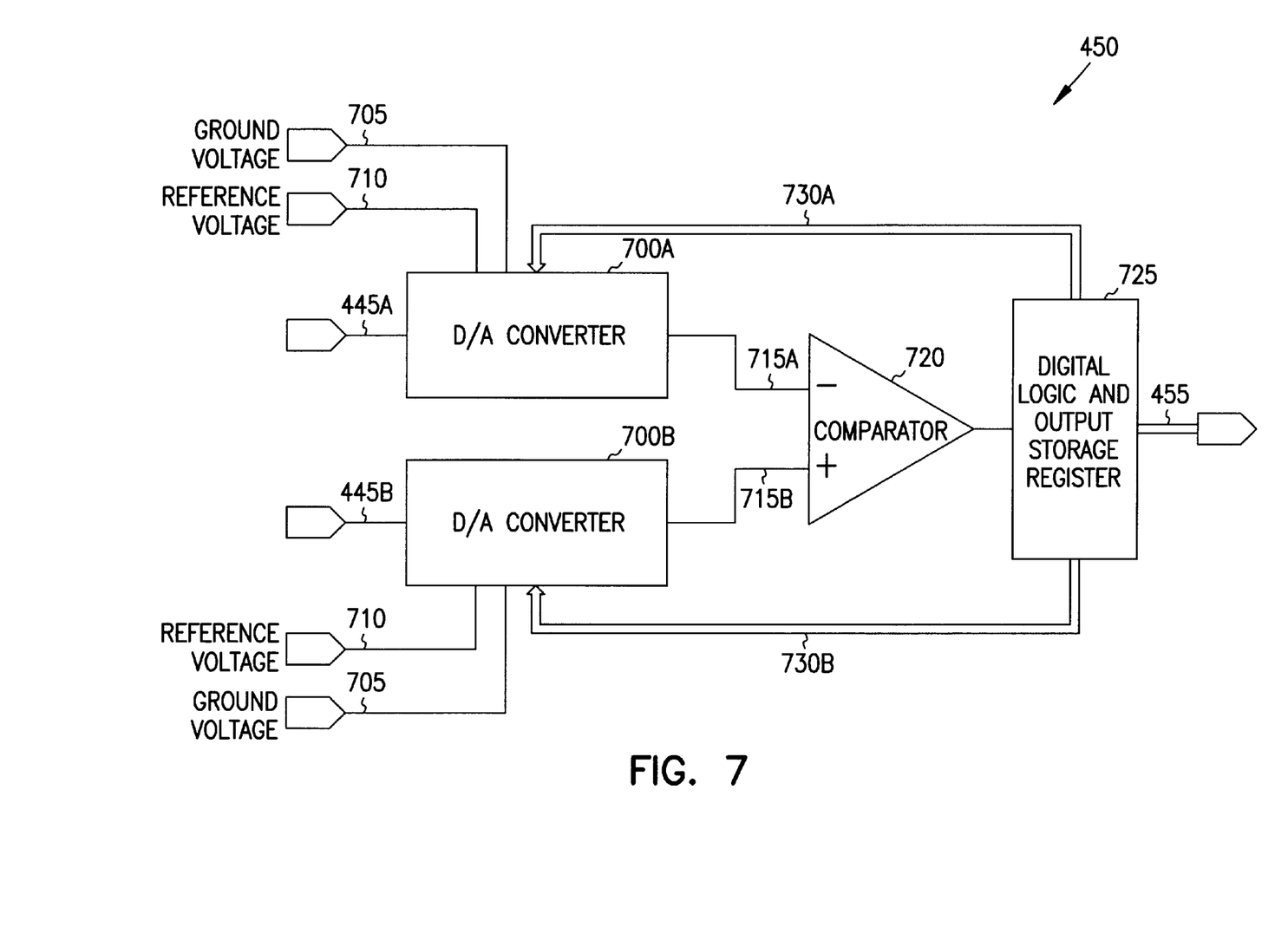
FIG. 7 is a schematic/block diagram illustrating generally one embodiment of portions of an analog-to-digital (A/D) converter.

FIG. 7 is a schematic/block diagram illustrating generally, by way of example, but not by way of limitation, one embodiment of portions of A/D converter 450 for performing analog-to-digital conversion of the differential input signal at nodes 445A–B. Each of the signals at nodes 445A–B is received at a respective one of digital-to-analog (D/A) converters 700A–B. In one embodiment, each D/A converter 700A–B includes an 8-bit switched-capacitor successive approximation capacitor array that algorithmically switches particular capacitors in a binary-scaled capacitor array between a ground voltage, at nodes 705, and a reference voltage, at nodes 710. In this way, the input voltages at nodes 445A are individually combined with a scaled reference voltage to produce, at one of nodes 715A–B, an input voltage to comparator 720. Comparator 720 successively approximates the 8 bits (or other number of bits, depending on the desired signal resolution) of the digital output signal for storage in a storage register in block 725. Block 725 also includes control logic for controlling the successive approximation algorithms of D/A converters 700A–B via nodes/busses 730A–B. An example of successive approximation A/D and D/A conversion is found in "Design of Analog-Digital VLSI Circuits For Telecommunication and Signal Processing," 296–306, (Jose E. Franca & Yannis Tsividis, eds., Prentice Hall 2d ed. 1994), which is herein incorporated by reference.

Operational Transconductance Amplifier

Figure 8:
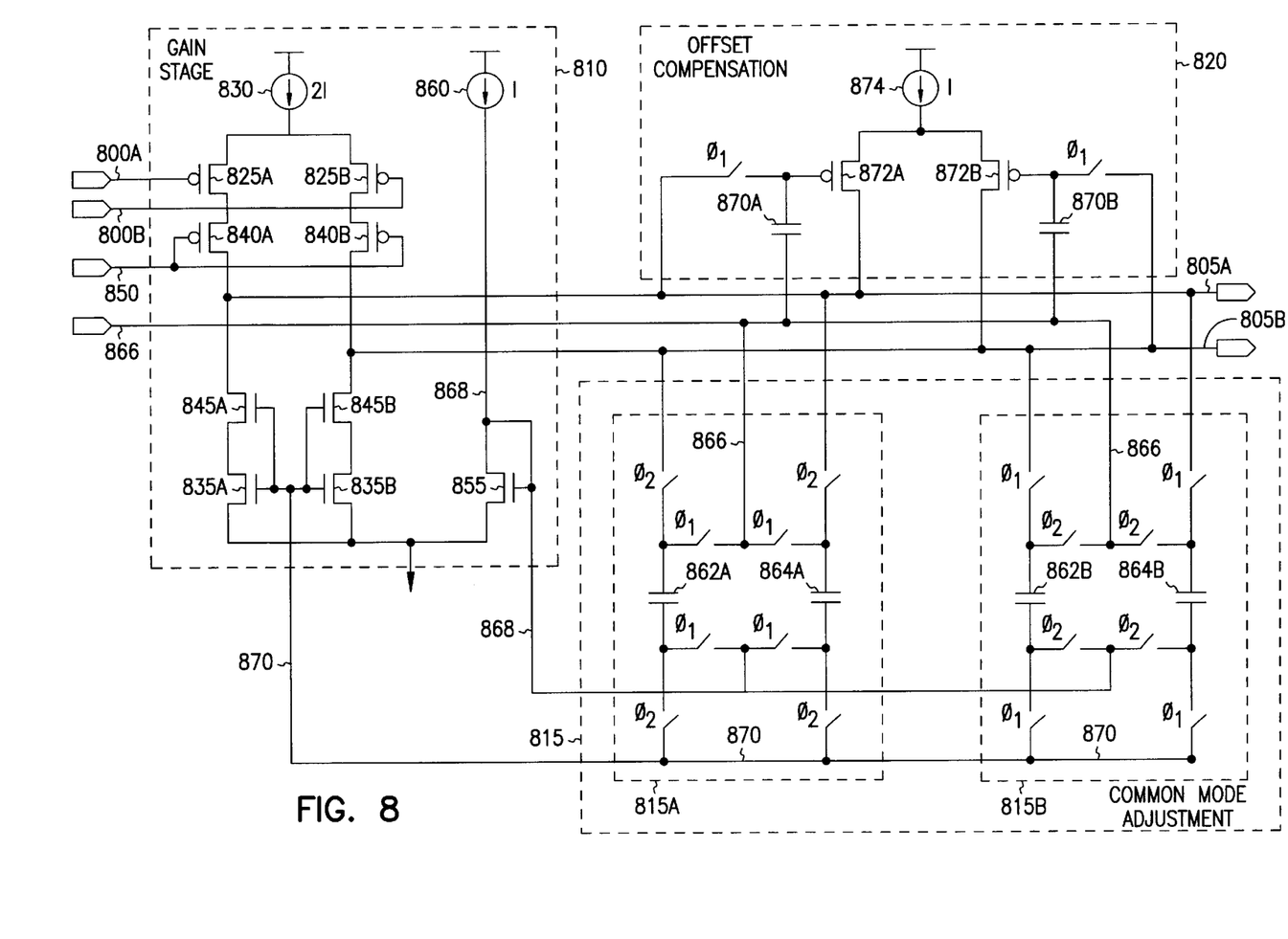
FIG. 8 is a schematic diagram illustrating generally one embodiment of portions of an amplifier, such as an operational transconductance amplifier (OTA).

FIG. 8 is a schematic diagram illustrating generally, by way of example, but not by way of limitation, one embodiment of portions of an amplifier, such as operational transconductance amplifier (OTA) 515. In this embodiment, OTA 515 includes differential first and second inputs at nodes 800A–B and differential first and second outputs at nodes 805A–B. OTA 515 includes differential-voltage-to-differential-current converting gain stage 810, a common mode adjustment circuit 815 including first and second common mode adjustment subcircuits 815A–B, and an offset compensation circuit 820.

In one embodiment, gain stage 810 includes first and second transconductance devices 825A–B, receiving the first and second input signals at nodes 800A–B, respectively. In this example, transconductance devices 825A–B are p-channel field-effect transistors, i.e., "PFETs"), which steer the current provided by current source 830 to one or the other of current source/sink devices 835A–B (e.g., n-channel field-effect transistors, i.e., "NFETs"). The output impedance of OTA 515 is increased by the presence of cascoding devices 840A–B (e.g., PFETs) and 845A–B (e.g., NFETs). Cascoding device 840A–B and 845A–B are separately biased by predetermined bias voltages at nodes 850 and 870, respectively. OTA 515 also includes a diode-connected transistor 855 (e.g., NFET), biased by current source 860. Diode-connected transistor 855 provides a gate bias voltage for driving the gates of current sink devices 835A–B. In this example, transistor 855 delivers the gate bias voltage to current sink devices 835A–B not directly, but through common-mode adjustment circuit 815, as discussed below.

Output common mode adjustment circuit 815 establishes operating voltages at output nodes 805A and 805B to accommodate the differential-input/differential-output topology of OTA 515. Without common mode adjustment circuit 815, the current delivered by current source 830 through each leg (i.e., through transconductor 825A in the first leg and through transconductor 825B in the second leg) of gain stage 810 may not exactly match the current sunk by the corresponding current sink device 835A–B. As a result, the output voltages at output nodes 805A–B might drift high or low. But by providing common mode adjustment circuit 815, stable bias voltages are established at output nodes 805A–B. Common mode adjustment circuit 815 includes two common mode adjustment subcircuits 815A–B, which alternatingly provide bias voltages at output nodes 805A–B during different clock phases.

First common mode adjustment subcircuit 815A provides bias voltages at output nodes 805A–B during $\phi_2$. First, during $\phi_1$, capacitors 862A and 864A are each charged up to the voltage difference between a predetermined reference voltage, at node 866, and the desired gate bias voltage for current sinks 835A–B, which is provided by the drain/gate voltage of diode-connected device 855 at node 868. Then, during $\phi_2$, each of capacitors 862A and 864A is coupled between its corresponding output node 805B–A, respectively, and node 870, which provides a bias voltage to current sink devices 835A–B. This establishes the bias voltage at node 870 to be approximately equal to the voltage at node 868 during $\phi_2$, which, in turn, establishes the bias voltage at output nodes 805A–B to be approximately equal to the predetermined reference voltage at node 866 during $\phi_2$.

Second common mode adjustment subcircuit 815B provides bias voltages at output nodes 805A–B during $\phi_1$. First, during $\phi_2$, capacitors 862B and 864B are each charged up to the voltage difference between a predetermined reference voltage, at node 866, and the desired gate bias voltage for current sinks 835A–B, which is provided by the drain/gate voltage of diode-connected device 855 at node 868. Then, during $\phi_1$, each of capacitors 862B and 864B is coupled between its corresponding output node 805B–A, respectively, and node 870, which provides a bias voltage to current sink devices 835A–B. This establishes the bias voltage at node 870 to be approximately equal to the voltage at node 868 during $\phi_2$, which, in turn, establishes the bias voltage at output nodes 805A–B to be approximately equal to the predetermined reference voltage at node 866 during $\phi_2$.

Offset compensation circuit 820 compensates for the offset voltage of OTA 515. Without offset compensation circuit 820, the output voltages at output nodes 805A–B may not be equal even when the input voltages at input nodes 800A–B are equal. This offset voltage may result from, among other things, a mismatch in transconductance and/or threshold voltages of input transconductance devices 825A–B. During $\phi_1$, when the input nodes 800A–B are held, by switches outside OTA 515, at input voltages that are approximately identical to each other, the difference between the output voltages at 805A–B and the predetermined reference voltage at node 866 are stored on respective capacitors 870A–B. During $\phi_2$, the switches that coupled capacitors 870A–B to respective output nodes 805A–B during $\phi_1$ are opened up. The offset voltage that was stored on capacitors 870A–B during $\phi_1$ appears across the inputs of differential pair devices 872A–B (e.g., PFETs). Based on this stored offset voltage, devices 872A–B steer current provided by current source 874 to one or the other of the first leg of gain stage 810, which includes current sink device 835A, and the second leg of gain stage 810, which includes current sink device 835B. The difference in currents provided by devices 872A–B through the large signal impedance of the first and second legs of gain stage 810 reduces the intrinsic offset voltage between at output nodes 805A–B.

Power Savings of Present System

The cardiac rhythm management system example described above with respect to FIGS. 1–8 provides a differential signal processing channel that offers several advantages. Among other things, it allows power savings, such as through the use of lower bias currents in the active circuits (e.g., OTAs 515) used in the discrete time signal processing. This saves energy, thereby extending the useful life of the battery-powered implanted device 105 before explantation and replacement becomes necessary.

Figure 9:
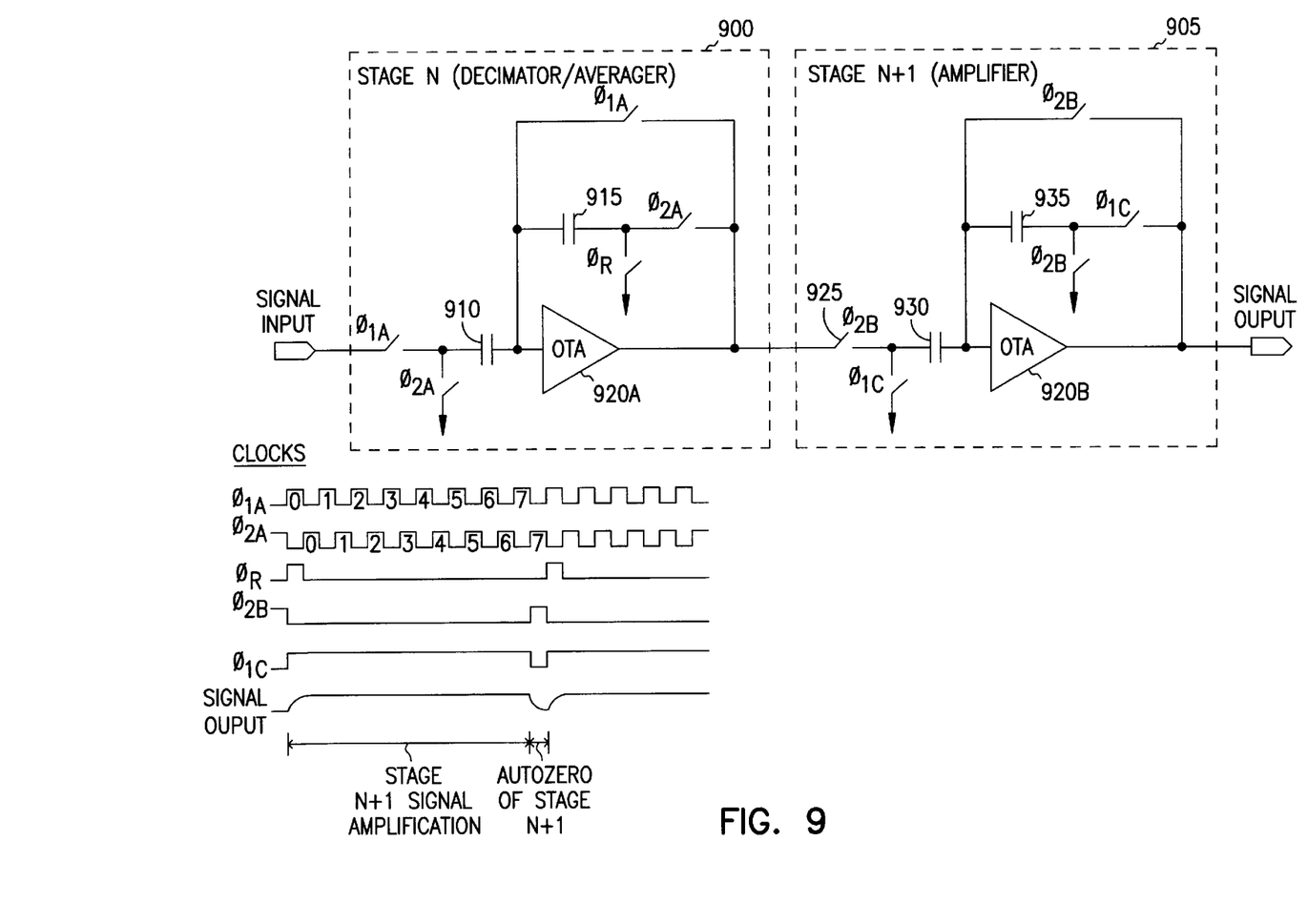
FIG. 9 is a schematic diagram illustrating generally portions of a single-ended signal processing channel and accompanying clocks.

One aspect of this power savings is best understood by comparison to a portion of a single-ended discrete time signal processing channel illustrated generally in FIG. 9 together with an illustration of clocks used therein, $\phi_{1A}$, $\phi_{2A}$, $\phi_R$, $\phi_{2B}$ and $\phi_{1C}$(the corresponding switches are closed when the associated clock is "high" and open when the clock is "low."). FIG. 9 includes two discrete time signal processing stages, e.g., Stage N, such as a decimator/averager 900, and Stage N+1, such as amplifier 905 (amplifier 905 may also be understood as the sampling and feedforward integration portion of a single-ended highpass filter). In this example, decimator/averager 900 samples eight successive inputs onto input capacitor 910 during successive clock periods $\phi_{1A}$, and averages these eight successive input samples onto integration capacitor 915 during successive clock periods $\phi_{2A}$ before resetting the integration capacitor 915 during the reset clock phase $\phi_R$.

In this example, the output from decimator/averager 900 is sampled directly onto the input of OTA 920B in amplifier 905 through switch 925 and capacitor 930 during clock phase $\phi_{2B}$. Because OTA 920B includes an intrinsic input offset voltage, it is "autozeroed" during clock phase $\phi_{2B}$, i.e., the input offset voltage of OTA 920B is stored on integration capacitor. In this example, because the output from decimator/averager 900 is sampled directly onto the input of OTA 920B, as described above, the autozeroing must occur during the same short time period as the input sampling, e.g., during $\phi_{2B}$. Moreover, this short time period determines the bias current that must be used in OTA 920B to obtain the desired degree of settling during the short time period of $\phi_{2B}$. During actual signal amplification by amplifier 905 during $\phi_{1C}$, which is the complement of clock $\phi_{2B}$, power is being wasted because the signal output settles much faster than it needs to because OTA 920B is designed to settle within the much shorter autozeroing time period of clock $\phi_{2B}$, as illustrated by the signal output example in FIG. 9. In this example, clock $\phi_{2B}$ has a $\frac{1}{16}$ duty cycle that is efficiently utilized during autozero, while clock $\phi_{1C}$ has a $\frac{15}{16}$ duty cycle, only $\frac{1}{16}$ of which is being efficiently utilized during signal amplification by amplifier 905. Similarly, the roles of $\phi_{2B}$ and $\phi_{1C}$ could be interchanged, in which case the signal amplification phase would have a duty cycle of $\frac{1}{16}$ that is efficiently utilized, while the autozero phase would have a duty cycle of $\frac{15}{16}$, only $\frac{1}{16}$ of which would be efficiently utilized. Thus, in FIG. 9, the speed of Stage N+1 must be comparable to the speed of Stage N, which dictates that Stage N+1 must have approximately the same amount of bias current as Stage N.

However, the downsampling by decimation/averager 900 provides a lower valid data output frequency than its input sampling frequency. Because Stage N has a lower output data frequency than its input sampling frequency, a properly designed subsequent Stage N+1 can use a lower bias current if, for example, its duty cycle is more evenly divided into ½ for amplification and ½ for autozeroing, rather than $\frac{1}{16}$ for autozeroing and $\frac{15}{16}$ for autozeroing as in the example described above (for a decimation by a factor of eight). In such a design, the lower frequency and more even duty cycle of Stage N+1 implies that a significantly reduced current may be used in the active circuits of Stage N+1 and any subsequent signal processing stages.

In FIG. 6A, for example, amplifier/highpass filter 435A is designed to take advantage of such potential bias current savings. In FIG. 6A, the output signal from decimator/averager 425 is not coupled directly onto OTA 515 in feedforward integration circuit 605, but is rather coupled only onto the input capacitors in input/sampling circuit 600 during $\phi_{2B}$. Switches are closed during $\phi_{4B}$ to couple the inputs of OTA 515 in feedforward integration circuit 605 to a reference or ground voltage while the input signal is being sampled during $\phi_{2B}$. As seen in the clock diagram in FIG. 5, this allows the full downsampled frequency to be more evenly divided between signal amplification, during $\phi_{3B}$, and autozeroing, during $\phi_{4B}$, each of which alternately share a ½ duty cycle in this example. Because more time is available for signals to settle during both autozeroing and signal amplification, the OTAs 515 in feedforward integration circuit 605 and feedback integration circuit 610 can be designed to use less bias current, thereby saving power and prolonging the usable life of implanted device 105. Similarly, amplifier 435B in FIG. 6B operates at the lower downsampled frequency with substantially evenly divided duty cycles of amplification and autozeroing, allowing its OTAs 515 to be biased as less current, further contributing to power savings. Another advantage of the differential signal processing arrangement illustrated in FIGS. 5, 6A, and 6B is that charge injection (also called clock feedthrough) of switches coupled to the inputs of the OTAs 515 is substantially canceled by the presence of switches on each of the inputs of OTAs 515. This balancing minimizes the effect of clock feedthrough since it appears as a common mode input signal to the OTAs 515, and will be rejected according to the common mode rejection capabilities of the OTAs 515.

Conclusion

This document describes, among other things, portions of a differential signal processing channel for differentially processing signals, such as cardiac signals in an implantable cardiac rhythm management device. The differential signal processing channel offers many advantages over single-ended discrete-time processing of cardiac signals using conventional autozeroing techniques. For example, the above-described differential signal processing techniques allow the use of lower bias currents in the active circuits used in discrete time signal processing. This saves power, thereby extending the useful life of the implanted device before explantation and replacement becomes necessary. The differential signal processing techniques also reduce the effects of clock feedthrough of the switches used in the switched-capacitor circuits, provide a wider dynamic range for the cardiac signals being acquired, and provide better rejection of power supply noise. This document also describes an operational transconductance amplifier (OTA), capable of use in the discrete-time differential signal processing channel. The OTA provides, among other things, an output common mode adjustment circuit and an offset compensation circuit.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A cardiac rhythm management system including:
   an implantable cardiac rhythm management (CRM) device, adapted to be coupled to first and second cardiac sensing electrodes, the CRM device including:
   an interface circuit, including first and second inputs adapted to be respectively coupled to the first and second cardiac sensing electrodes, and including first and second outputs providing an analog differential output signal based on the signals at the first and second inputs; and
   a discrete-time differential signal processing channel, including first and second inputs respectively coupled to receive the analog differential output signal from the first and second outputs of the interface circuit and providing a digitized output signal based at least in part on the analog differential output signal received from the first and second outputs of the interface circuit.

2. The system of claim 1, in which the signal processing channel includes a filter.

3. The system of claim 2, in which the filter includes a decimator/averager.

4. The system of claim 3, in which the signal processing channel includes an amplifier.

5. The system of claim 4, in which at least one of the filter and the amplifier includes an operational transconductance amplifier (OTA).

6. The system of claim 5, in which the OTA includes a common mode adjustment circuit.

7. The system of claim 5, in which the OTA includes an offset compensation circuit.

8. The system of claim 1, in which the signal processing channel includes switched-capacitor circuitry.

9. The system of claim 1, in which the interface circuit includes a substantially linear amplifier.

10. The system of claim 1, further including a programmer adapted to be remotely communicatively coupled to the CRM device.

11. The system of claim 1, further including first and second cardiac sensing electrodes.

12. A cardiac rhythm management system including:

first and second cardiac sensing electrodes; and an implantable cardiac rhythm management (CRM) device, coupled to the first and second cardiac sensing electrodes, the CRM device including:

a linear amplifier circuit, including first and second inputs respectively coupled to the first and second cardiac sensing electrodes, and including first and second outputs providing a differential linear amplifier circuit output signal based on the signals at the first and second inputs;

a switched-capacitor differential signal processing channel, including first and second inputs respectively coupled to receive the linear amplifier circuit output signal from the first and second outputs of the linear amplifier circuit and providing a digitized output signal based at least in part on the linear amplifier circuit output signal, the signal processing channel including:

a decimator/averager circuit, including first and second inputs respectively coupled to receive the analog differential output signal from the first and second outputs of the linear amplifier circuit, and including first and second outputs providing a differential decimator/averager output signal based at least in part on the analog differential output signal received from the linear amplifier circuit;

a switched-capacitor (SC) amplification circuit, including first and second inputs respectively coupled to receive the decimator/averager output signal from the first and second outputs of the decimator/averager circuit, and including first and second outputs providing a differential SC amplification circuit output signal based at least in part on the decimator/averager output signal; and an analog-to-digital (A/D) converter circuit, including first and second inputs respectively coupled to receive the SC amplification circuit output signal from the first and second outputs of the amplification circuit, and including an output bus providing a digitized signal based at least in part on the SC amplification circuit output signal.

13. The system of claim 12, in which at least one of the decimator/averager circuit and the SC amplification circuit includes an operational transconductance amplifier (OTA) circuit including:

a common mode adjustment circuit; and an offset correction circuit.

14. A method of acquiring cardiac signals, the method comprising:

receiving cardiac signals at first and second cardiac electrodes;

communicating the cardiac signals to an implantable cardiac rhythm management device;

buffering the cardiac signals received from the first and second cardiac electrodes to provide a differential buffered signal;

processing, differentially and in discrete-time, the differential buffered signal; and providing a digitized output signal based on the processed differential buffered signal.

15. The method of claim 14, in which processing the differential buffered signal includes:

decimating/averaging the differential buffered signal to provide a decimated/averaged signal; and amplifying the decimated/averaged signal.

16. The method of claim 15, in which at least one of decimating/averaging and amplifying includes:

receiving a differential input voltage between first and second inputs;

providing a differential output current, based on the differential input voltage, at first and second outputs;

adjusting a common mode output voltage at the first and second outputs; and compensating for an offset in the differential output current at the first and second outputs.

17. The method of claim 15, further including remotely programming at least one operating parameter of cardiac rhythm management device.

18. A cardiac rhythm management system including an implantable cardiac rhythm management (CRM) device, adapted to be coupled to first and second cardiac sensing electrodes, the CRM device including a discrete-time differential signal processing channel, including:

first and second inputs;

a decimator/averager, providing a downsampled differential decimator/averager output signal based on signals at the first and second inputs; and an amplifier/filter, receiving the decimator/averager output signal and providing an amplifier/filter differential output signal based thereon, the amplifier/filter including autozeroing and amplification phases of substantially equal time duration.

19. The system of claim 18, in which the amplification phase includes valid data being provided by the amplifier/filter at the frequency of the downsampled differential/averager output signal.

20. A cardiac rhythm management system including:

an implantable cardiac rhythm management (CRM) device, adapted to be coupled to first and second cardiac sensing electrodes, the CRM device including:

an interface circuit, including first and second inputs adapted to be respectively coupled to the first and second cardiac sensing electrodes, and including first and second outputs providing an analog differential output signal based on the signals at the first and second inputs; and a discrete-time differential signal processing channel, including first and second inputs respectively coupled to receive the analog differential output signal from the first and second outputs of the interface circuit and providing a digitized output signal based at least in part on the analog differential output signal received from the first and second outputs of the interface circuit, and in which the signal processing channel includes a decimator/averager.

21. The system of claim 20, in which the signal processing channel includes an amplifier.

22. The system of claim 21, in which at least one of the decimator/averager and the amplifier includes an operational transconductance amplifier (OTA).

23. The system of claim 22, in which the OTA includes a common mode adjustment circuit.

24. The system of claim 22, in which the OTA includes an offset compensation circuit.

25. A cardiac rhythm management system including:

an implantable cardiac rhythm management (CRM) device, adapted to be coupled to first and second cardiac sensing electrodes, the CRM device including:
- an interface circuit, including first and second inputs adapted to be respectively coupled to the first and second cardiac sensing electrodes, and including first and second outputs providing an analog differential output signal based on the signals at the first and second inputs; and
- a discrete-time differential signal processing channel, including first and second inputs respectively coupled to receive the analog differential output signal from the first and second outputs of the interface circuit and providing a digitized output signal based at least in part on the analog differential output signal received from the first and second outputs of the interface circuit, and in which the signal processing channel includes a downsampler circuit.

26. The system of claim 25, in which the signal processing channel includes an amplifier.

27. The system of claim 25, in which at least one of the downsampler and the amplifier includes an operational transconductance amplifier (OTA).

28. The system of claim 27, in which the OTA includes a common mode adjustment circuit.

29. The system of claim 27, in which the OTA includes an offset compensation circuit.

* * * * *